United States Patent
Hettler

(10) Patent No.: US 11,205,569 B2
(45) Date of Patent: Dec. 21, 2021

(54) GLASS-METAL FEEDTHROUGH

(71) Applicant: Schott AG, Mainz (DE)

(72) Inventor: Robert Hettler, Kumhausen (DE)

(73) Assignee: Schott AG, Mainz (DE)

( * ) Notice: Subject to any disclaimer, the term of this patent is extended or adjusted under 35 U.S.C. 154(b) by 0 days.

(21) Appl. No.: 17/075,322

(22) Filed: Oct. 20, 2020

(65) Prior Publication Data

US 2021/0043439 A1 Feb. 11, 2021

Related U.S. Application Data

(63) Continuation of application No. 16/516,507, filed on Jul. 19, 2019.

(30) Foreign Application Priority Data

Jul. 20, 2018 (DE) .................. 10 2018 005 733.0

(51) Int. Cl.
*H01B 17/30* (2006.01)
*H01J 61/36* (2006.01)
(Continued)

(52) U.S. Cl.
CPC ............ *H01J 61/366* (2013.01); *B60R 21/26* (2013.01); *B60R 22/34* (2013.01); *C03C 27/02* (2013.01);
(Continued)

(58) Field of Classification Search
CPC .................................................. H01J 61/366
(Continued)

(56) References Cited

U.S. PATENT DOCUMENTS 3,770,568 A 11/1973 Graff et al.
5,709,724 A * 1/1998 Naugler .................. C03C 27/02
65/59.4

(Continued)

FOREIGN PATENT DOCUMENTS

DE 198 42 943 A1 3/2000
EP 1 028 923 * 9/1997
EP 1 028 923 B1 11/2004

OTHER PUBLICATIONS

Wang et al., Nickel-Free Duplex Stainless Steels, Jul. 17, 1998, Scripts Materials, vol. 40, No. 1, pp. 123-129 (Year: 1998).*

(Continued)

*Primary Examiner* — Stanley Tso
(74) *Attorney, Agent, or Firm* — Taylor IP, P.C.

(57) ABSTRACT

A glass-metal feedthrough includes: an external conductor including steel, having a coefficient of expansion $\alpha_{external}$, and having an opening formed therein; an internal conductor disposed in the opening, the internal conductor including steel and having a coefficient of expansion $\alpha_{internal}$. The external conductor and the internal conductor are configured to not release nickel when in contact with a human or animal body or biological cells of a cell culture. A glass material surrounds the internal conductor within the opening and has a coefficient of expansion $\alpha_{glass}$. The coefficient of expansion $\alpha_{external}$ of the external conductor and the coefficient of expansion $\alpha_{internal}$ of the internal conductor both are greater than the coefficient of expansion $\alpha_{glass}$ of the glass material.

9 Claims, 1 Drawing Sheet

(51) Int. Cl.
*H01M 50/186* (2021.01)
*H01M 50/191* (2021.01)
*B60R 21/26* (2011.01)
*B60R 22/34* (2006.01)
*C03C 27/02* (2006.01)
*F42B 3/107* (2006.01)
*F42B 3/198* (2006.01)

(52) U.S. Cl.
CPC .......... *F42B 3/107* (2013.01); *H01B 17/305* (2013.01); *H01M 50/186* (2021.01); *H01M 50/191* (2021.01); *B60R 2021/26029* (2013.01); *F42B 3/198* (2013.01)

(58) Field of Classification Search
USPC .................................................. 174/152 GM
See application file for complete search history.

(56) References Cited

U.S. PATENT DOCUMENTS

| | | | | |
|---|---|---|---|---|
| 6,278,896 | B1* | 8/2001 | Stehlik | A61N 1/05 174/152 GM |
| 2003/0207168 | A1* | 11/2003 | Gan | H01M 4/131 429/50 |
| 2004/0014582 | A1* | 1/2004 | Budd | C03C 8/24 501/5 |
| 2011/0031698 | A1* | 2/2011 | Tziviskos | A61N 1/3754 277/312 |
| 2015/0325821 | A1* | 11/2015 | Bradwell | H01M 2/08 429/101 |
| 2016/0049781 | A1* | 2/2016 | Nisslbeck | H01B 1/02 174/650 |
| 2017/0092907 | A1* | 3/2017 | Hyung | H01M 2/30 |
| 2018/0050211 | A1* | 2/2018 | Hausch | H02G 15/013 |
| 2020/0353268 | A1 | 11/2020 | Yang et al. | |
| 2021/0020862 | A1* | 1/2021 | Nishiguchi | H01L 51/5004 |

OTHER PUBLICATIONS

Yang et al., Nickel-Free austenitic stainless steels for medical appliations, Dec. 2009, Science and Technology of Advanced Materials, 11 (2010) 014105 (Year: 2009).*

Yang et al. ("Nickel-free austenitic stainless steels for medical applications", Institute of Metal Research, Feb. 26, 2010, "Yang" (Year: 2010).* https://www.engineeringtoolbox.com/linear-expansion-coefficients-d_95.html, accessed on Mar. 26, 2021 (Year: 2021).*

European Office Action dated Dec. 2, 2019 for European Patent Application No. 19 17 4825 (4 page).

European Search Report dated Dec. 2, 2019 for European Patent Application No. 19174825.0-1124 (6 pages).

Yong, Practical Handbook for Modern Continuous Steel Casting, Metallurgical Industry Press, Mar. 2010, Section 6.1.1, 1st Edition, Beijing (1 page).

* cited by examiner d/D
INVENTION
AISI 430 CONDUCTOR d/D
STATE OF THE ART
KOVAR CONDUCTOR

GLASS-METAL FEEDTHROUGH

CROSS-REFERENCE TO RELATED APPLICATIONS

This is a continuation of U.S. patent application Ser. No. 16/516,507 entitled "GLASS-METAL FEEDTHROUGH," filed Jul. 19, 2019, which is incorporated herein by reference.

BACKGROUND OF THE INVENTION

1. Field of the Invention

The invention relates to a glass-metal feedthrough, consisting of an external conductor, a glass material and an internal conductor and to the use thereof in a medical device, in particular in an implantable medical device and relates also to equipment, and devices having such glass-metal feedthroughs.

2. Description of the Related Art

Glass-metal feedthroughs are used in diverse areas of application in electrical engineering. They are used, for example, for sealing of electric conductors into housings for components in electronics and sensor technology. In this context, such components feature fusion seals of glasses with various metal materials. By fusing an internal conductor consisting of metal into a glass or glass ceramic material which is surrounded by an external conductor consisting of metal, a hermetically sealed feedthrough of a conductor in a housing can be provided. Particularly special glass-metal feedthroughs are such feedthroughs wherein the feedthrough itself or parts of the feedthrough come into contact with the human body. With such feedthroughs it is important that high corrosion resistance and long-term stability of all utilized components can be ensured. In particular, such feedthroughs should only emit limited amounts of Ni in order to prevent formation of allergic reactions. This is defined in the standards for the permissible limits of so-called nickel release. Reference is hereby made to DIN EN1811 and DIN EN12472.

In glass-metal feedthroughs, Fe—Ni, Fe—Ni—Co, Fe—Ni—Cr alloys are predominantly used for the feedthrough conductor. The advantage of these materials is their excellent adaptability of the thermal expansion to the sealing glasses. However, all of these materials have significant amounts of Ni in the base material. They are furthermore nickel coated to protect the materials against corrosion, which in turn causes release of undesirable amounts of nickel.

In order to prevent Ni release, it was provided in the current state of the art to coat the feedthrough conductor or, respectively, the internal conductor with a sufficiently thick gold layer to reduce nickel permeation. This however, had the disadvantage that prevention of nickel leakage was insufficient and in order to achieve satisfactory prevention, very thick Au-layers with a thickness of more than 2.5 μm were necessary.

As an alternative to a solution featuring coated conductors, DE 198 42 943 A1 suggests as the closest prior art, to use a tantalum internal conductor or alternatively a nickel-free, non-corrosive and ferritic high grade stainless steel, for example the steel according to US-Standard AISI 446 which is a non-corrosive heat-resistant ferritic chrome steel with aluminum addition. The coefficient of expansion of the ferritic high grade stainless steel AISI 446 is only slightly higher than that of common glasses. Therefore, there is a danger that, during cooling the internal conductor contracts more than the glass and the interface with the glass ruptures. An additional disadvantage of DE 198 42 943 A1 is, that the selection of Ni-free materials was limited, since a sufficiently tight seal of the feedthrough can only be provided if the coefficient of expansion of the internal conductor $\alpha_{internal}$ was less than the coefficient of expansion of the glass $\alpha_{glass}$.

A glass composition has become known from U.S. Pat. No. 3,770,568 A which can be used for hermetically sealed tantalum electrolytic capacitors and which comprises an effective chrome content in the glass composition.

What is needed in the art is a glass-metal feedthrough which permits a wider selection of materials for the internal conductor and an effectively sealed feedthrough.

In particular, internal conductors should be possible which, on the one hand, do not release nickel when in contact with the human body and, on the other hand, offer sufficient sealability.

SUMMARY OF THE INVENTION

An exemplary embodiment of a glass-metal feedthrough provided in accordance with the present invention is characterized in that a coefficient of expansion of an internal conductor $\alpha_{internal}$ is greater than a coefficient of expansion of the glass $\alpha_{glass}$, the coefficient of expansion of an external conductor $\alpha_{external}$ is greater than the coefficient of expansion of the glass $\alpha_{glass}$, and the external conductor and the internal conductor comprise steel and are configured to not release nickel when in contact with a human or animal body or biological cells of a cell culture Compressive pre-stressing of the external conductor upon the glass achieves that the glass also exerts positive pressure (joint pressure) upon the glass to the internal conductor interface. This results in the advantage that that pressure reliably maintains a tightly sealed connection. Moreover, a low height of the glass-metal feedthrough is achieved which can be used for diverse applications such as devices for monitoring of patients or arm bands in the leisure sector.

The restriction to a greater expansion of the pin as internal conductor relative to glass, and an expansion of the external conductor relative to glass of at least greater than 2 ppm/K is particularly effective on highly expandable materials for the pin, with an expansion of greater than 10 ppm/K. Hardly any good sealing glasses are available in this range.

It has been surprisingly found that, for example, use of ferritic high grade stainless steel with high chrome content of between 10.5 and 20%, such as a high grade stainless steel with a chrome content of 15 to and 17%, for example ferritic high grade stainless steel AISI 430 is possible. As an alternative to the ferritic high grade stainless steels other materials such as molybdenum, tungsten or platinum can also be used. These additional materials also have a low allergy potential. The inventive condition $\alpha_{internal} > \alpha_{glass}$ for the coefficients of expansion must also apply to these materials, wherein $\alpha_{internal}$ is the coefficient of expansion of the internal conductor and $\alpha_{glass}$ is the coefficient of expansion of the glass.

A problem in the use of these steels is however, that their thermal coefficient of expansion $\alpha_{internal}$ at 11.6 to 11.5 $10^{-6}$/K is higher than the coefficient of expansion of the glass $\alpha_{glass}$ which is in the range of 10.6 to 6.1 $10^{-6}$/K. It has been surprisingly found that in spite of a greater $\alpha_{internal}$ of the conductor which is above that of $\alpha_{glass}$—in contrast to the current state of the art which dictates that with glass-metal feedthroughs the thermal expansion of the internal conductor must not be greater than that of the used glass, in order to provide a sufficiently tight seal—a tight glazed seal is also provided in the event that $\alpha_{internal}$ is greater than $\alpha_{glass}$ if a positively high joint pressure that is applied by the external conductor upon the glass is provided. As was demonstrated on further examination, it is not sufficient for a tight seal if the joint pressure is merely positive; in fact a joint pressure greater than 30 MPa, such as greater than 50 MPa or greater than 100 MPa must be attained to achieve a reliable glazed seal.

Such a high joint pressure is provided in the case of $\alpha_{internal}$ being less than $\alpha_{glass}$, if sufficient compressive pre-stressing is applied upon the glass by the external conductor. The thus resulting joint pressure between glass and internal conductor then occurs during cooling of the feedthrough after sealing. If this joint pressure is clearly positive, that is greater than 30 MPa, greater than 50 MPa, or greater than 100 MPa, the transition between glass and metal—that is, the transition from glass to the internal conductor—remains closed and therefore tightly sealed, even though $\alpha_{internal}$ is less than $\alpha_{glass}$. The joint pressure is directly dependent on the expansion differential. Moreover, dependencies on the inventive geometry are also conceivable. The joint pressure is a surface pressure. The joint pressure expresses the force per unit surface area with which a first body presses upon a second body.

In order to generate the necessary joint pressure, the difference between the coefficient of expansion of the external conductor $\alpha_{external}$ and the coefficient of expansion of the glass is at least 2 ppm/K, such as at least 4 ppm/K, wherein the coefficient of expansion is greater than the coefficient of expansion of the glass $\alpha_{glass}$. In some embodiments, the glass $\alpha_{glass}$ of the internal conductor is selected in such a manner that the coefficient of expansion of the internal conductor $\alpha_{internal}$ is 1.1 times greater than the coefficient of expansion $\alpha_{glass}$ of the glass. In some embodiments, $\alpha_{internal}$ is in the range of $1.1 \cdot \alpha_{glass}$ to $2 \cdot \alpha_{glass}$. In order to apply the necessary pressure of the external conductor onto the glass material and to ensure a tight seal, it is provided that the external conductor consists of a nickel-free, non-corrosive, chemically stable steel (high grade stainless steel). The coefficient of expansion of the external conductor is greater than that of the glass in order to provide the necessary joint pressure.

In some embodiments, the external conductor is made of austenitic steel, such as high grade stainless steel 316L which is characterized by good sealability and a high coefficient of expansion.

In addition to the nickel-free ferritic high grade stainless steel, in particular the non-hardenable ferritic high grade steel with a high chrome content whose coefficient of expansion $\alpha_{internal}$ is greater than that of the glass material the use of molybdenum, tungsten or platinum for the internal conductor is also conceivable.

The coefficients of expansion may be selected so that a joint pressure at the internal conductor of at least 30 MPa, such as at least 50 MPa or at least than 100 MPa is provided.

In addition to the feedthrough, exemplary embodiments of the invention also provide for the use of the glass-metal feedthrough in implantable medical devices or equipment, as well as providing an element that can be inserted into, or attached to the human or animal body or biological living cells containing cell cultures, said element having a glass-metal feedthrough, wherein the external conductor and the internal conductor—at least in the regions which come into contact with the human or animal body—consist of metals having a reduced allergy potential. In some embodiments, the external conductor as well as the internal conductor consist of these metals.

The metal of the external and the internal conductor can come into contact with the human or animal body or the cell cultures and are characterized in that they do not release any nickel and/or chrome.

The metal of the external and internal conductor—at least in the surface areas which during operation come into contact with the human or animal body, or with biological cells of the cell culture—may consist of nickel-free and/or chrome-free steels.

Especially suitable as metals for the internal conductor—at least in the surface areas which during operation come into contact with the human or animal body, or with biological cells of the cell culture—are metals selected from the group of the ferritic high grade stainless steels, platinum, platinum/iridium, niobium, titanium, molybdenum, tungsten as well as combinations thereof. The ferritic high grade stainless steels comprise AISI 4xx-groups, for example AISI 430.

The metals for the internal conductor—at least in the surface areas which during operation come into contact with the human or animal body, or with biological cells of the cell culture—may be selected from the group:
AISI 316 L
AISI 430
AISI 630
as well as combinations thereof. Additional materials for the external conductors can be selected from the group of austenitic high grade stainless steels AISI 3xx or ferritic high grade stainless steels AISI 4xx.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
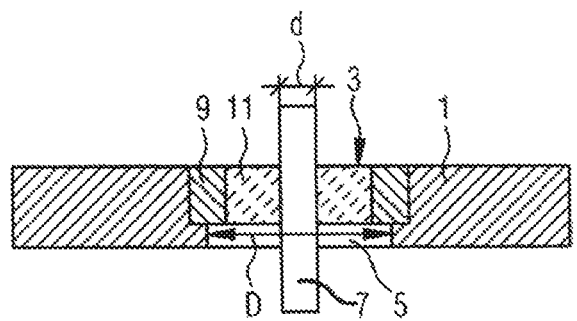
FIG. 1 is a schematic illustration of an exemplary embodiment provided in accordance with the present invention.

FIG. 1 is a schematic depiction of a cross section through an exemplary embodiment provided in accordance with the invention. In the glass-metal feedthrough through a housing 1 illustrated in FIG. 1 which may be made of aluminum, a feedthrough 3 is inserted into an opening 5 in housing 1. Feedthrough 3 includes a feedthrough conductor or respectively an internal conductor 7 which is inserted into an external conductor 9. External conductor 9 may also be referred to as base body and may consist of an austenitic high grade stainless steel with a high thermal coefficient of expansion. The external conductor may also be referred to as base body and is joined with the housing, by, for example, welding. The internal conductor is glazed centrally into the external conductor or feedthrough conductor 7. This is achieved in that internal conductor 7 in an insulating glass body 11, completely fills the space inside external conductor 9. The glass into which the internal conductor 7 is fused may be a bio-compatible glass.

Also illustrated in FIG. 1 is diameter d of feedthrough conductor 7, as well as the so-called hole diameter D of opening 5.

According to the invention it is provided that the glass has a coefficient of expansion $\alpha_{glass}$, that the internal conductor has coefficient of expansion $\alpha_{internal}$ and that the external conductor has a coefficient of expansion $\alpha_{external}$. The materials are selected in such a manner, that the coefficient of expansion of the internal conductor $\alpha_{internal}$ is greater than that of the glass $\alpha_{glass}$. The difference between the coefficient of expansion of the external conductor and the coefficient of expansion of the glass is at least 2 ppm/K, such as at least 4 ppm/K. The coefficient of expansion of the external conductor $\alpha_{external}$ in the temperature range of 20° C. to the transformation temperature is greater than the coefficient of expansion $\alpha_{glass}$. Thus, a joint pressure is provided at the internal conductor of at least 30 MPa, such as of at least 50 MPa or of at least 100 MPa.

Figure 2A:
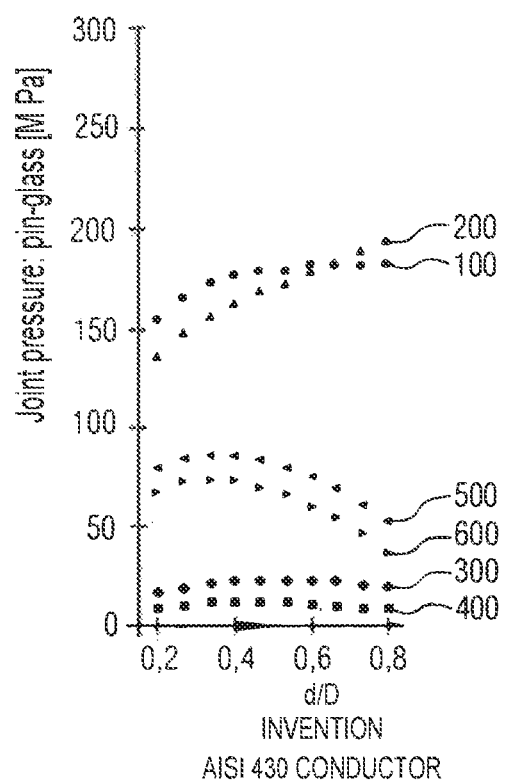
FIG. 2A is a flow chart of joint pressure of conductor and glass.

If, as demanded by the invention, the coefficient of expansion of the internal conductor $\alpha_{internal}$ is greater than that of the glass $\alpha_{glass}$, it will become problematic to provide a sufficiently tightly sealed feedthrough. In such a case, a sufficiently tight seal is ensured only if the external conductor can generate a sufficiently high joint pressure upon the glass. The joint pressure is relevant to d/D according to the state of the art is illustrated in FIG. 2A. Kovar which, with an a of 7.3 to 6.6 $10^{-6}$ l/K is slightly above the value of the coefficient of expansion $\alpha_{glass}$ and which is not covered by the invention was used as the material for the feedthrough conductor. d indicates the diameter of the conductor and D the diameter of opening 5. d/D specifies the relationship between the diameter of conductor d and hole diameter D. Generally, small d/D values characterize the large gap between conductor and opening and large d/D values characterize a small gap between conductor and opening.

The feedthroughs according to FIG. 2A are hermetically sealed. They however have the disadvantage that Kovar alloys have a high nickel content, so that nickel could be released from the feedthrough conductors.

Thus, it is provided according to the present invention to replace the Kovar feedthrough conductor with a material which does not release nickel. Surprisingly it was found that a material suitable for this purpose is a ferritic, Ni-free high grade stainless steel, in particular AISI 430. The disadvantage with a Ni-free high grade stainless steel, for example AISI 430 is however, that $\alpha_{internal}$ is at 11.5·$10^{-6} K^{-1}$ and is thus clearly above the coefficient of expansion $\alpha_{glass}$ of the glass material. The coefficient of expansion of the used glasses $\alpha_{glass}$ is namely in a range of 6.1·$10^{-6} K^{-1}$ to 10.6·$10^{-6} K^{-1}$.

In order to achieve a pressure tight glazed seal with such a constellation, a sufficiently high joint pressure which is applied by the external conductor must be generated.

Figure 2B:
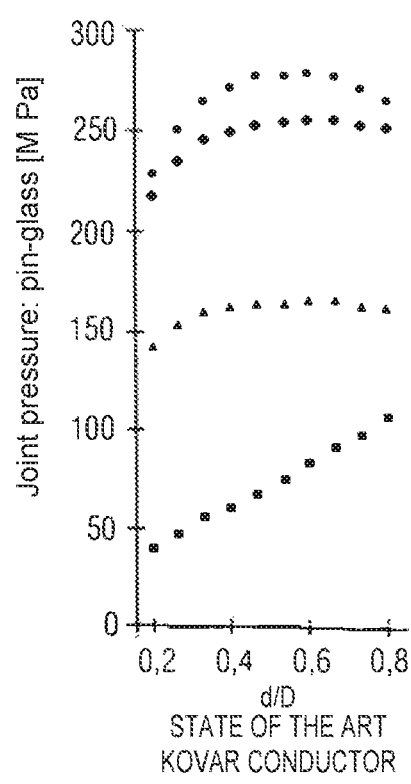
FIG. 2B is a flow chart of joint pressure of conductor and glass.

The joint pressure for feedthroughs of this type is illustrated in FIG. 2B and is relevant to d/D.

As can be seen from FIG. 2B, a sufficiently high joint pressure for the use of AISI 430 as material for the feedthrough component results, especially if the external conductor consists of an austenitic high grade stainless steel with a $\alpha_{external}$ of 18.3 $10^{-6}$/K. Such composition provides a sufficiently high joint pressure to ensure a tight seal. The joint pressure of such a material combination is identified with reference numbers 100 and 200. The joint pressure increases with a larger d/D and thus small gap, to values of above 150 MPa.

Curves 300 and 400 describe the joint pressure for an AISI 430 feedthrough conductor, wherein the external conductor is AISI 430 or AISI 630 and wherein the glass has a coefficient of expansion of 10.6·$10^{-6}$ and is thus within the range of the coefficient of expansion of the external conductor as well as that of the feedthrough conductor. Because of this, the necessary joint pressure cannot be generated. Such material combinations generally demonstrate a low joint pressure. Curves 300 and 400 progress flat with little influence of the diameter due to the diameter ratio.

The materials of the different curves in the diagram according to FIG. 2B "joint pressure over d/D" are specified in the table below:

| Curve | External material | External CTE to TG | Glass Tg in ° C. | Glass CTE to Tg | Conductor Material | Conductor CTE to TG | Symbol |
|---|---|---|---|---|---|---|---|
| 200 | AISI316L | 18.3 | 525 | 10.6 | AISI430 | 11.5 | ● |
| 100 | AISI316L | 18.4 | 565 | 6.1 | AISI430 | 11.6 | ▲ |
| 600 | AISI430 | 11.5 | 525 | 10.6 | AISI430 | 11.5 | ■ |
| 400 | AISI430 | 11.6 | 565 | 6.1 | AISI430 | 11.6 | ▶ |
| 300 | AISI630 | 11.4 | 525 | 10.6 | AISI430 | 11.5 | ◆ |
| 500 | AISI630 | 11.4 | 565 | 6.1 | AISI430 | 11.6 | ◀ |

The material components of curves 100, 300 show an especially high joint pressure, so that a hermetic seal of the feedthrough is provided.

The specified glass-metal feedthroughs can be used in implantable medical devices or equipment. They can be produced cost effectively and are characterized by very low Ni release. Because of the high joint pressure they moreover are hermetically sealed—in other words feature a helium leakage of less than 1·$10^{-8}$ mbar/sec.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A glass-metal feedthrough, comprising:
an external conductor comprising steel, having a coefficient of expansion $\alpha_{external}$, and having an opening formed therein;
an internal conductor disposed in the opening, the internal conductor comprising steel and having a coefficient of expansion $\alpha_{internal}$, the external conductor and the internal conductor being configured to not release nickel when in contact with a human or animal body or biological cells of a cell culture; and a glass material surrounding the internal conductor within the opening and having a coefficient of expansion $\alpha_{glass}$, the coefficient of expansion $\alpha_{external}$ of the external conductor and the coefficient of expansion $\alpha_{internal}$ of the internal conductor both being greater than the coefficient of expansion $\alpha_{glass}$ of the glass material, wherein the coefficient of expansion of the internal conductor $\alpha_{internal}$ is 1.7 times to 4 times greater than the coefficient of expansion of the glass material $\alpha_{glass}$, wherein the coefficient of expansion of the internal conductor $\alpha_{internal}$ and the coefficient of expansion of the external conductor $\alpha_{external}$ are such that a joint pressure of at least 30 MPa is generated on a portion of the internal conductor in contact with the glass material in a temperature range of 20° C. to a glass transformation temperature of the glass material, wherein a difference between the coefficient of expansion of the external conductor $\alpha_{external}$ and the coefficient of expansion of the glass material $\alpha_{glass}$ is at least 2 ppm/K in the temperature range of 20° C. to the glass transformation temperature of the glass material, wherein the external conductor and the internal conductor both comprise AISI 316L steel.

2. The glass-metal feedthrough of claim 1, wherein the coefficient of expansion of the external conductor $\alpha_{external}$ is 1.1 times to 4 times greater than the coefficient of expansion of the glass material $\alpha_{glass}$.

3. The glass-metal feedthrough of claim 1, wherein the glass material seals the internal conductor in the opening of the external conductor.

4. A glass-metal feedthrough, comprising:
an external conductor having a coefficient of expansion $\alpha_{external}$, and having an opening formed therein;
an internal conductor disposed in the opening,
the internal conductor comprising AISI 316L steel and having a coefficient of expansion $\alpha_{internal}$,
the external conductor and the internal conductor being configured to not release nickel when in contact with a human or animal body or biological cells of a cell culture; and
a glass material surrounding the internal conductor within the opening and having a coefficient of expansion $\alpha_{glass}$,
the coefficient of expansion $\alpha_{external}$ of the external conductor and the coefficient of expansion $\alpha_{internal}$ of the internal conductor both being greater than the coefficient of expansion $\alpha_{glass}$ of the glass material,
wherein the coefficient of expansion of the internal conductor $\alpha_{internal}$ is 1.7 times to 4 times greater than the coefficient of expansion of the glass material $\alpha_{glass}$,
wherein the coefficient of expansion of the internal conductor $\alpha_{internal}$ and the coefficient of expansion of the external conductor $\alpha_{external}$ are such that a joint pressure of at least 30 MPa is generated on a portion of the internal conductor in contact with the glass material in a temperature range of 20° C. to a glass transformation temperature of the glass material,
wherein a difference between the coefficient of expansion of the external conductor $\alpha_{external}$ and the coefficient of expansion of the glass material $\alpha_{glass}$ is at least 2 ppm/K in the temperature range of 20° C. to the glass transformation temperature of the glass material,
wherein the external conductor and the internal conductor both consist of AISI 316L steel.

5. The glass-metal feedthrough of claim 4, wherein the coefficient of expansion of the external conductor $\alpha_{external}$ is 1.1 times to 4 times greater than the coefficient of expansion of the glass material $\alpha_{glass}$.

6. The glass-metal feedthrough of claim 4, wherein the glass material seals the internal conductor in the opening of the external conductor.

7. An element for insertion into or attachment to a human or animal body or biological cells of a cell culture, the element comprising:
a glass-metal feedthrough comprising:
an external conductor comprising steel, having a coefficient of expansion $\alpha_{external}$, and having an opening formed therein;
an internal conductor disposed in the opening,
the internal conductor comprising AISI 316L steel and having a coefficient of expansion $\alpha_{internal}$,
the external conductor and the internal conductor being configured to not release nickel when in contact with the human or animal body or the biological cells of the cell culture; and
a glass material surrounding the internal conductor within the opening and having a coefficient of expansion $\alpha_{glass}$,
the coefficient of expansion $\alpha_{external}$ of the external conductor and the coefficient of expansion $\alpha_{internal}$ of the internal conductor both being greater than the coefficient of expansion $\alpha_{glass}$ of the glass material,
wherein the coefficient of expansion of the internal conductor $\alpha_{internal}$ is 1.7 times to 4 times greater than the coefficient of expansion of the glass material $\alpha_{glass}$,
wherein the coefficient of expansion of the internal conductor $\alpha_{internal}$ and the coefficient of expansion of the external conductor $\alpha_{external}$ are such that a joint pressure of at least 30 MPa is generated on a portion of the internal conductor in contact with the glass material in a temperature range of 20° C. to a glass transformation temperature of the glass material,
wherein a difference between the coefficient of expansion of the external conductor $\alpha_{external}$ and the coefficient of expansion of the glass material $\alpha_{glass}$ is at least 2 ppm/K in the temperature range of 20° C. to the glass transformation temperature of the glass material,
wherein the external conductor and the internal conductor both comprise AISI 316L steel.

8. The element of claim 7, wherein at least one of the external conductor or the internal conductor consists of AISI 316L steel.

9. The element of claim 7, wherein the coefficient of expansion of the external conductor $\alpha_{external}$ is 1.1 times to 4 times greater than the coefficient of expansion of the glass material $\alpha_{glass}$.

* * * * *